United States Patent [19]

Liao

[11] Patent Number: 5,487,502
[45] Date of Patent: Jan. 30, 1996

[54] DECORATIVE MEANS FOR EMITTING ODOR AND GENERATING SOUND

[76] Inventor: Ming-Kang Liao, c/o Hung Hsing Patent Service Center, P.O. Box 55-1670, Taipei, Taiwan

[21] Appl. No.: 280,086

[22] Filed: Jul. 25, 1994

[51] Int. Cl.$^6$ ....................................................... A61L 9/04
[52] U.S. Cl. ............................ 239/69; 239/211; 222/648; 222/78
[58] Field of Search ............................. 239/69–72, 211, 239/34; 222/509, 333, 645–649, 78, 330

[56] References Cited

U.S. PATENT DOCUMENTS

| | | | |
|---|---|---|---|
| 1,701,032 | 7/1927 | Dubray | 239/211 |
| 1,947,353 | 2/1934 | Mueller | 239/211 |
| 2,991,912 | 7/1961 | Thomas et al. | 239/70 X |
| 3,589,563 | 6/1971 | Carragan | 239/70 X |
| 3,739,944 | 6/1973 | Rogerson | 239/70 X |
| 4,407,585 | 10/1983 | Hartford et al. | 368/12 |
| 5,221,025 | 6/1993 | Privas | 222/1 |
| 5,254,028 | 10/1993 | Liao | 446/297 |

Primary Examiner—Kevin P. Weldon

[57] ABSTRACT

A decorative device includes a main body for holding a decorative article in the main body, a container for filling a compressed fluid for producing odors or fragrance in the container, a driving device for opening and closing a releasing valve of the container as controlled by a control device, a discharge pipe connected to the container, a plurality of nozzles divergently branched from the discharge pipe and widely distributed in the decorative article, and a sound generating device electrically connected to the control device and mounted in the main body, whereby upon actuation of the control device, the releasing valve of the container will be opened by the driving device to spray vapor or gas of the fluid through the nozzles distributed in the decorative article for providing a smell (preferably a fragrant smell) from the decorative article and also for producing sound from the sound generating device for enhancing a decorative effect.

1 Claim, 4 Drawing Sheets

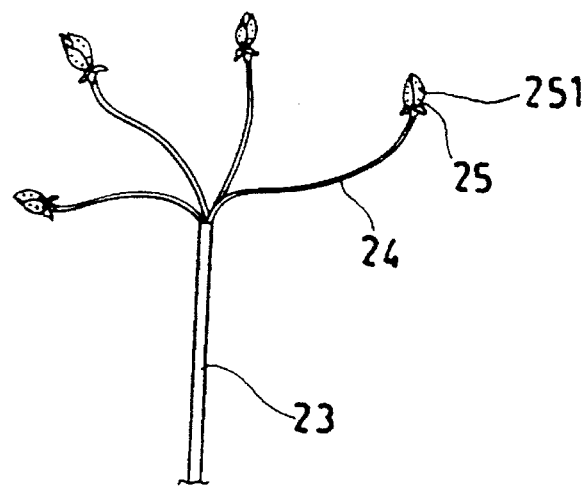
F I G. 3A
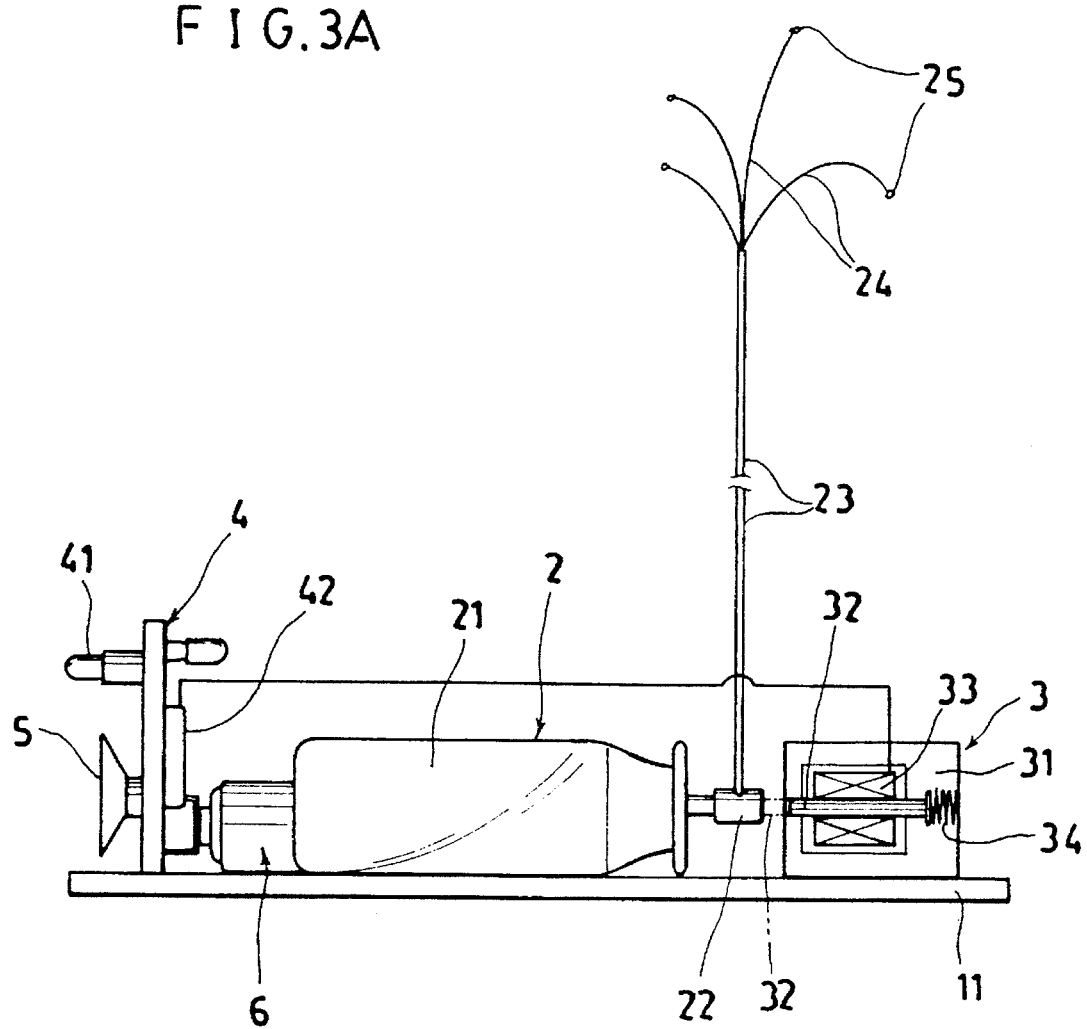
F I G. 3

DECORATIVE MEANS FOR EMITTING ODOR AND GENERATING SOUND

BACKGROUND OF THE INVENTION

A fluid releasing and sound generating toy of U.S. Pat. No. 5,254,028 granted to the same inventor of this application includes a toy body, a container, an electric valve, a tube, a sound generating unit, a receiving circuit and a controller unit, whereby upon actuation of the controller unit, an electrical signal will be received by the receiving circuit to activate the electric valve to release the compressed fluid from the container, and to activate the sound generating unit for sound generation simultaneously.

The compressed fluid for producing fragrant gas or pungent gas is directly and instantly released from a fluid discharge hole T3 formed in a toy body T when the electric valve 2 is opened. There is no suitable medium or mechanism provided for distributing or delivering the discharged fluid to a broader area to be circumferentially disposed on a decorative body if the toy of U.S. Pat. No. 5,254,028 is inferentially modified to be a decorative item, thereby limiting the uses of the toy of U.S. Pat. No. 5,254,028.

SUMMARY OF THE INVENTION

The object of the present invention is to provide a decorative device including a main body for holding a decorative article in the main body, a container for filling a compressed fluid having odor or fragrant smell in the container, a driving device for opening and closing a releasing valve of the container as controlled by a control device, a discharge pipe connected to the container, a plurality of nozzles divergently branched from the discharge pipe and widely distributed in the decorative article, and a sound generating device electrically connected to the control device and mounted in the main body, whereby upon actuation of the control device, the releasing valve of the container will be opened by the driving device to spray vapor or gas through the nozzles distributed in the decorative article for providing a smell (preferably fragrant smell) from the decorative article and also for producing sound from the sound generating device for enhancing a decorative effect.

BRIEF DESCRIPTION OF THE DRAWINGS

FIG. 3 shows an odor distributing system in accordance with the present invention.

FIG. 3A is an illustration showing the nozzles for simulating the flower buds of the present invention.

DETAILED DESCRIPTION

Figure 1:
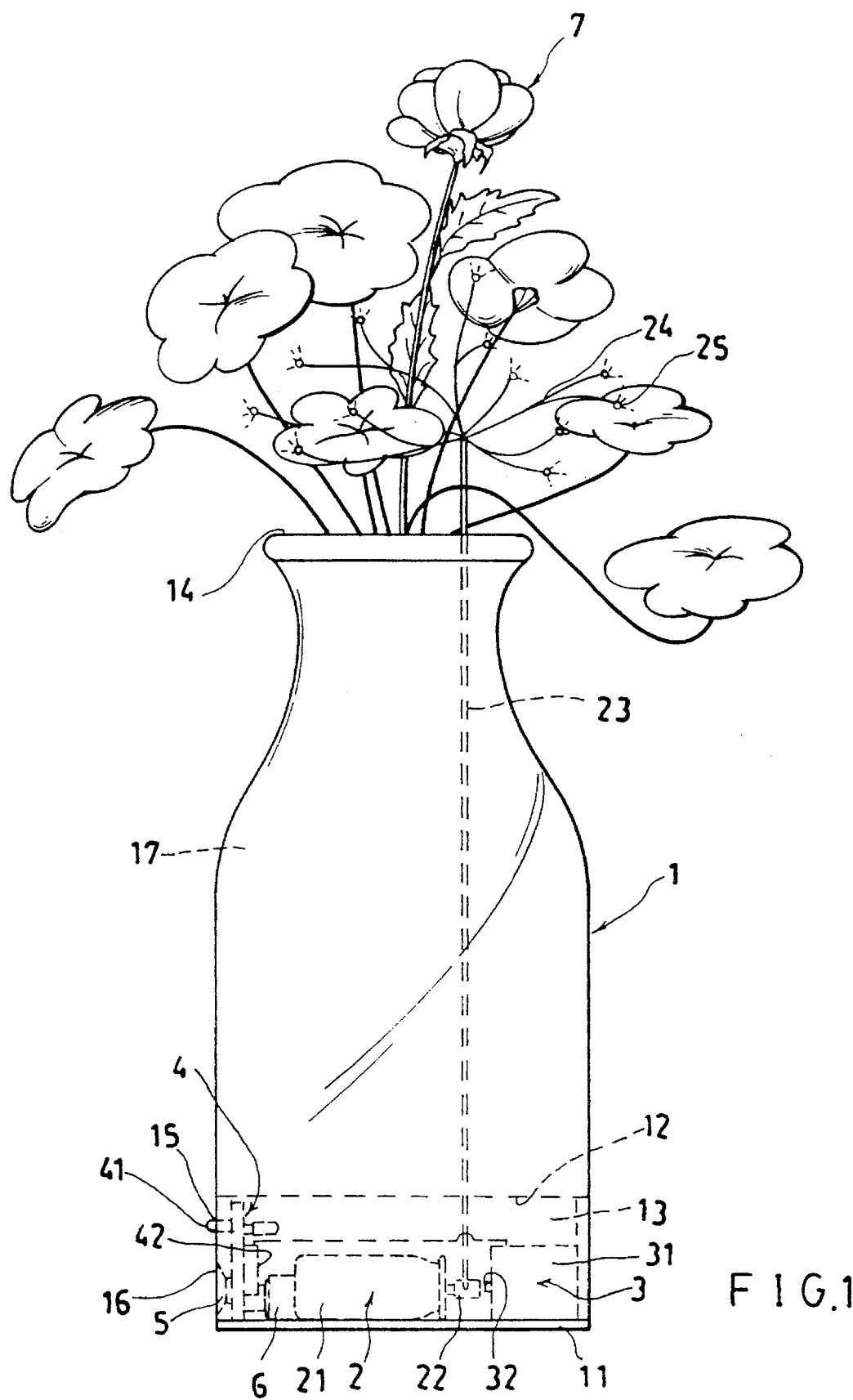
FIG. 1 is an illustration of the present invention when assembled.
Figure 2:
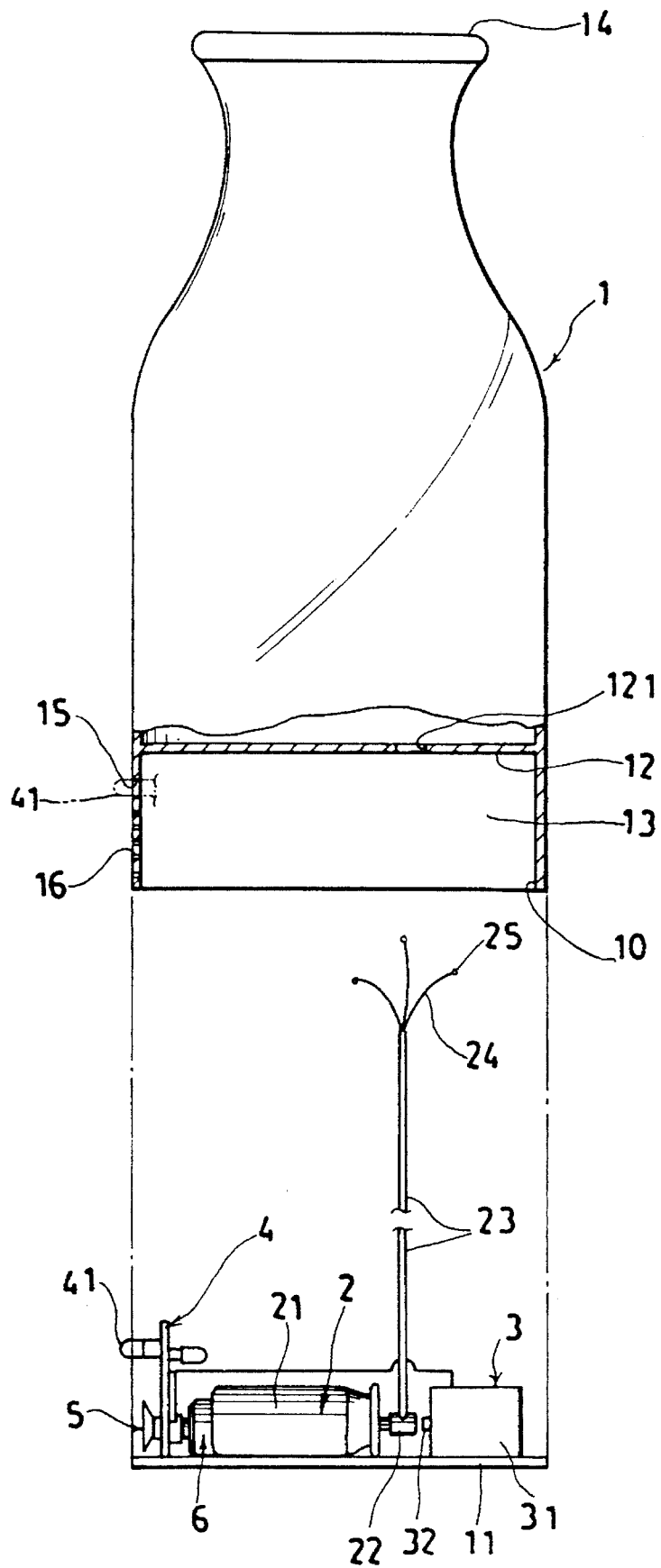
FIG. 2 is a partial exploded view of the present invention.

As shown in FIGS. 1–3, a decorative means of the present invention comprises: a main body 1, an odor distributing means 2, a driving means 3, a control means 4, a sound generating means 5, a power source 6, and a decorative article 7. The power source 6 may be a direct current from battery or batteries; or may be a power source of alternative current.

The main body 1 may be a vase or other holding devices and the decorative article 7 may be a bundle of flowers or an ornamental plant or any other ornamental articles, but not limited in this invention. The flower may be artificial or dried flower.

The main body 1 as shown in FIGS. 1 and 2 includes: a base plate 11 detachably sealing a bottom opening 10 of the main body 1 for mounting the odor distributing means 2, the driving means 3, the control means 4, the sound generating means with speaker 5 and the power source of battery or batteries 6 on the base plate 11, a partition plate 12 formed on a lower portion of the main body 1 and positioned above the base plate 11 for defining a lower chamber 13 between the two plates 12, 11 for storing the several means 3, 4, 5 and batteries 6 in the chamber 13, a top opening 14 formed in a top portion of the main body 1 and communicated with an upper chamber 17 formed in an upper portion of the main body 1 above the lower chamber 13.

The odor distributing means 2 includes: a container 21 filled with a compressed fluid capable of producing odors, preferably fragrant smells therein, a releasing valve 22 formed in a discharge pipe 23 connected to and communicated with the container 21 with the discharge pipe 23 protruding upwardly from the container 21 through a pipe hole 121 formed through the partition plate 12 in the main body 1, a plurality of capillary tubes 24 divergently distributed from an upper end of the discharge pipe 23 and protruding extrapolatively to be disposed in a wide area within the decorative article 7 as shown in FIG. 1, and a plurality of nozzles 25 each nozzle 25 terminated at one end of each capillary tube 24 and having a plurality of spraying perforations 251 drilled in each nozzle 25 and communicated with the tubes 24, the pipe 23 and the container 21 for spraying vapor, mist or fluid outwardly emitted from the container upon opening of the valve 22. Of course, the nozzles 25 and the tubes 24 may also be omitted.

The nozzles 25 may be formed as flower buds as shown in FIG. 3A or other shapes or structures for simultating a true flower, a plant or other decorative devices.

The driving means 3 as shown in FIG. 3 includes: a solenoid switch 31 mounted on the base plate 11 of the main body 1, a driving latch 32 slidably held in an electromagnetic coil 33 electrically connected to a control circuit 42 of the control means 4, a restoring spring 34 retained in the solenoid switch 31 and normally tensioning the latch 32 rearwardly, whereby upon powering of the electromagnetic coil 33, the latch 32 will be electromagnetically attracted forwardly to depress and open the releasing valve 22 of the container 21 to emit the compressed fluid to be sprayed outwardly through the nozzles 25.

The driving means 3 may be modified to use another type of valve opening and closing mechanism than illustrated in FIG. 3 for opening and closing of the valve 22.

The control means 4 electrically connected to the power source 6 includes a trigger 41, which may be a push button, a sensor, or other actuators, reciprocatively held in the main body 1; and a control circuit 42 which may be an integrated circuit or may include a timing circuit, whereby upon an actuation of the trigger 41, the timing circuit of the control circuit 42 may delay a time period for electrically energizing the coil 33 for attracting the latch 32 outwardly for continuously depressing and opening the releasing valve 22 in a pre-set time interval for emitting a pre-determined amount of fluid. The control or timing circuit of the control means 3 is not limited in this invention.

The trigger 41 may be made as a push button reciprocatively held in a trigger hole 15 formed in the main body 1. The trigger 41 may also be modified to be a remotely controlled trigger device (not shown).

The sound generating means 5 is electrically connected to the control circuit 42 of the control means 4 and includes a speaker mounted in the lower chamber 13 in the main body 1 for generating sound outwardly through speaker perforations 16 drilled in the main body 1.

When the trigger 41 of the control means 4 is actuated, the control circuit 42 will be initiated for activating the sound generating means 5 for producing sound, and for powering the electromagnetic coil 33 of the solenoid switch 31 for attracting the driving latch 32 forwardly to depress and open the releasing valve 22 for emitting compressed fluid from the container 21 for outwardly spraying vapor, mists or fluid through the nozzles 25 to be widely distributed on the decorative article 7. If the fluid is fragrant, this invention will be provided to vividly simulate a perfuming flower having a fragrance by shaping the decorative article 7 to be a flower or a bundle of flowers as shown in FIG. 1.

If the flower 7 of the present invention is a dried or artificial flower, it will now be "vitalized" because of its capability for emitting fragrant vapors, mists or fluid for simulating a true flower having fragrant smellings.

Figure 4:
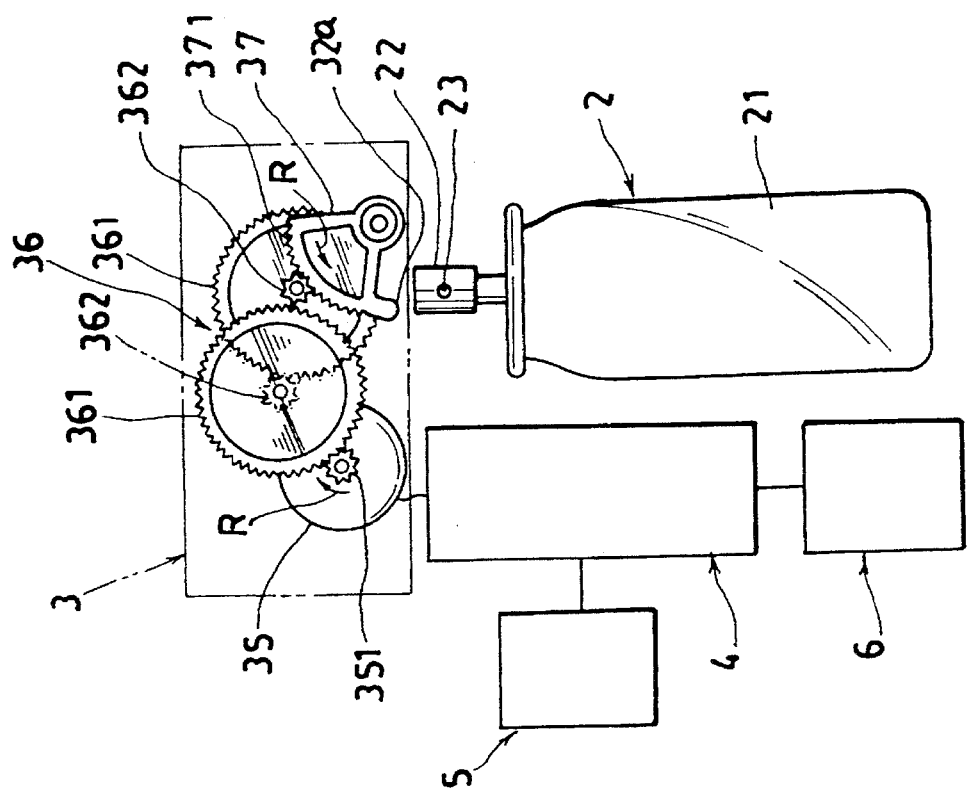
FIG. 4 shows another preferred embodiment of a driving means when opening the container valve of the present invention.
Figure 5:
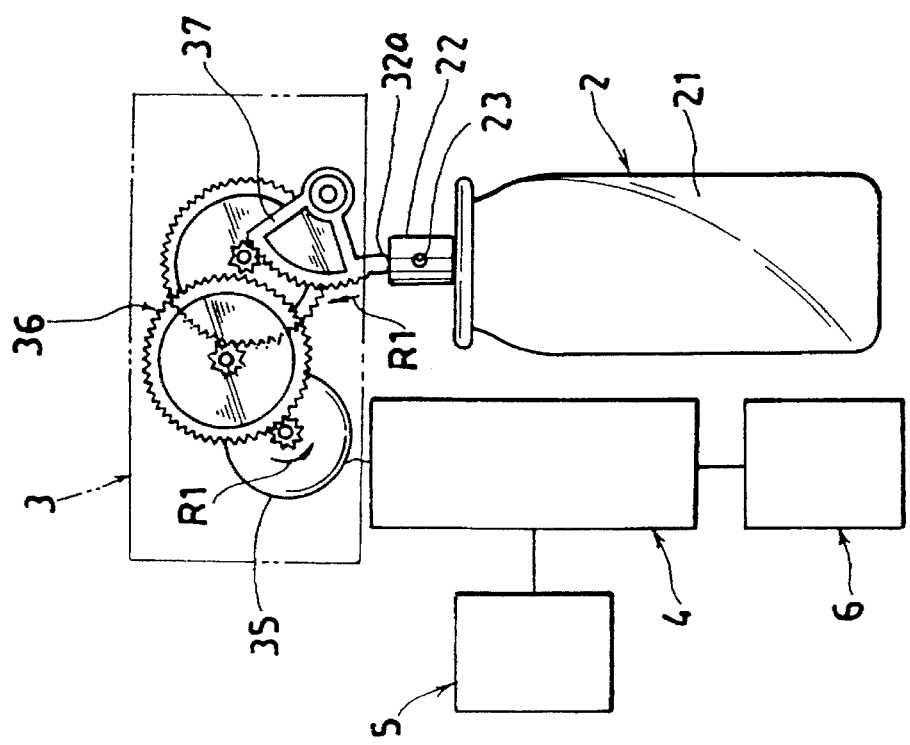
FIG. 5 shows the driving means of the present invention when closing the container valve, following the situation as shown in FIG. 4.

The driving means 3 of the present invention may be modified to be the preferred embodiment as shown in FIGS. 4 and 5, which includes: a driving motor 35 electrically connected to a control circuit 42 of the control means 4 and having a driving gear 351 secured to a motor shaft of the driving motor 35, a speed-reducing gear 36 having a large gear 361 engageable with the driving gear 351 of the driving motor 35 and a small gear 362 the number of gear teeth of the small gear 362 being smaller than that of the large gear 361 for reducing the speed of revolution of driving gear 35, a follower sector gear 37 having follower gear teeth 371 engageable with the small gear 362 of the speed-reducing gear 36, and a driving latch 32a protruding downwardly from a periphery of the sector gear 37 for depressing and opening the releasing valve 22 of the container 21 to emit compressed fluid outwardly upon forward rotation of the driving gear 351 and a counter-clockwise rotation (R) of the sector gear 37 as shown in FIG. 4. The control circuit 42 of the control means 4 may include a timing circuit for executing control sequences, upon actuation of the trigger 41 of the control means 4, first for counter-clockwise rotation of the driving gear 351 on the driving motor 35 which drives the sector gear 37 and latch 32a to open the releasing valve 22 of the container 21; then stopping the rotation of the driving motor 35 and latch 32a to continuously open the releasing valve 22 a pre-determined time period and finally for rotating the driving gear 351 clockwise by clockwise rotation of motor 35 causing the sector gear 37 and driving latch 32a to close the releasing valve 22 thereby stopping the emission and spray of compressed fluid from the container 21.

Other modifications may be made without departing from the spirit and scope of this invention.

I claim:

1. A decorative means comprising:

a main body having a decorative article held in said main body;

an odor distributing means mounted in said main body and having a container filled therein with a compressed fluid capable of producing odors and a discharge pipe connected to said container for emitting the compressed fluid towards said decorative article, a releasing valve in communication with said pipe for valving the fluid to said decorative article;

a driving means including: a solenoid switch mounted in the main body, a driving latch slidably held in an electromagnetic coil electrically connected to a control circuit of a control means, a restoring spring retained in the solenoid switch and normally tensioning the latch rearwardly, the electromagnetic coil operatively attracting the latch electromagnetically forwardly to depress and open the releasing valve of the container to emit the compressed fluid to be sprayed outwardly through at least one nozzle connected to said discharge pipe;

said control means electrically connected with a power source for powering said driving means for controlling the opening and closing of said releasing valve; and a sound generating means electrically connected with said control means and mounted in combination with said driving means in said main body, whereby upon triggering of said control means, said driving means will be actuated to open said releasing valve of said container for emitting the compressed fluid onto said decorative article for producing odor thereon, and said sound generating means will be simultaneously actuated for producing sound therefrom; the improvement which comprises:

said odor distributing means including a plurality of capillary tubes divergently distributed from an upper end of the discharge pipe and protruding outwardly from the discharge pipe to be disposed in a wide area within the decorative article, and a plurality of nozzles, each said nozzle at one end of each said capillary tube and having a plurality of spraying perforations drilled in each said nozzle for spraying fluid outwardly as emitted from said container upon opening of the releasing valve.

\* \* \* \* \*